US006179992B1

United States Patent
Näfe et al.

(10) Patent No.: US 6,179,992 B1
(45) Date of Patent: Jan. 30, 2001

(54) GAS SENSOR

(75) Inventors: Helfried Näfe, Stuttgart; Fritz Aldinger, Leinfelden-Echterdingen, both of (DE)

(73) Assignee: Max-Planck-Gesellschaft zur Förderung der Wissenschaften e.V., München (DE)

( * ) Notice: Under 35 U.S.C. 154(b), the term of this patent shall be extended for 0 days.

(21) Appl. No.: 09/202,407

(22) PCT Filed: Jun. 12, 1997

(86) PCT No.: PCT/EP97/03081

§ 371 Date: Dec. 14, 1998

§ 102(e) Date: Dec. 14, 1998

(87) PCT Pub. No.: WO97/47964

PCT Pub. Date: Dec. 18, 1997

(30) Foreign Application Priority Data

Jun. 12, 1996 (DE) ............................................. 196 23 487

(51) Int. Cl.$^7$ ................................................. G01N 27/407
(52) U.S. Cl. .......................... 205/781; 204/424; 204/426; 205/784; 205/786.5
(58) Field of Search .................... 204/421–429; 205/784, 785.5, 786.5, 781

(56) References Cited

U.S. PATENT DOCUMENTS

| 4,622,105 | * | 11/1986 | Liu et al. ............................... 204/424 |
| 4,715,944 | * | 12/1987 | Yanagida et al. ...................... 204/426 |
| 5,194,134 | * | 3/1993 | Futata et al. .......................... 204/421 |
| 5,755,940 | * | 5/1998 | Shindo ................................. 204/421 |

FOREIGN PATENT DOCUMENTS

| 0182921 A1 | 6/1986 | (EP) . |
| 0468249 A1 | 1/1992 | (EP) . |
| 0604243 A1 | 6/1994 | (EP) . |
| 9428403 | 12/1994 | (WO) . |
| WO95/34515 | * 12/1995 | (WO) . |

OTHER PUBLICATIONS

Potentiometric Gas Sensor for Carbon Dioxide . . . Electrolytes, Maruyama, et al, Solid State Ionics 23(1987) Month unavailable. 107–112.

Characteristics and sensing mechanism of . . . and metal sulphate, Yan, et al., Sensors and Actuators, B, 12, (1993), Month unavailable, pp. 77–81.

High–performance solid–electrolyte $SO_x$ sensor . . . auxiliary phase, Yan, et al., Sensors and Actuators, B, 20 (1994) Month unavailable, pp. 81–87.

Stabilized zirconia–based $NO_x$ sensor . . . at high temperature, Kurosawa, et al., Solid State Ionics 79 (1995) Month unavailable, pp. 338–343.

Mixed Potential Type $NO_x$ Sensor Based . . . and Oxide Electrode, Miura, et al., J. Electrochem. Soc. vol. 143, No. 2, Feb., 1996, pp. L33–L35.

(List continued on next page.)

Primary Examiner—T. Tung
(74) Attorney, Agent, or Firm—Fulbright & Jaworski, LLP

(57) ABSTRACT

The invention relates to a galvanic cell comprising
a) an oxygen-ion-conducting solid electrolyte,
b) a gas-sensitive material which contains at least one salt having the structural formula $Me_m(XO_n)_p$, where Me is a metal, X stands for C, S or N, and the symbols m, n and p characterize the respective stoichiometric relations,
c) a material, interposed between the oxygen-ion-conducting solid electrolyte and the gas-sensitive material, which allows conduction both by cations of the metal Me and by electrons and which seals off a potential-determining area of the solid electrolyte surface from the surroundings, making it impervious to gases therein, and
d) two electronically conductive potential taps at surface areas of the oxygen-ion-conducting solid electrolyte.

11 Claims, 3 Drawing Sheets

OTHER PUBLICATIONS

Solid–State Sensor for Sulfur Oxides Based on . . . Sulphate, Yan, et al., Chemistry Letters, 1992, Month unavailable, pp. 635–638.

Construction and Working Mechanism of Sulfur Dioxide . . . and Metal Sulfate, Nafe, J. Electrochem. Soc., vol. 143, No. 1, Feb. 1996—pp. 609–613.

Conclusions on the electronic conductivity of Na–β–alumina from the behavior . . . as electrolyte, Nafe, Solid State Ionics 68 (1994) Month unavailable 249–255.

Solid–State Potentiometric $CO_2$ sensors . . . and metal carbonate, Miura, et al., Sensors and Actuators, B24–25 (1995) Month unavailable, pp. 260–265.

New Types of Solid–Electrolyte Gas Sensors, Kleitz, et al., Fast Ion Transport in Solids (1979) Month unavailable.

Use of the Junction Between Two Solid . . . of Gaseous Oxides, Belanger, et al., J. Elect. Chem. Soc. vol. 131. No. 3, pp. 579–586 (Mar. 1984).

Recent Developments of the sensors for Carbon . . . Electrolytes, Saito, et al., Solid State Ionics, 28–30 (1998) Month unavailable 1644–1647) pp. 1645–1647.

Potentiometric Gas Sensor for Carbon . . . Electrolytes, Murayama, et al, Solid State Ionics 23 (1987) Month unavailable pp. 107–112.

Conclusions on the electronic conductivity of Na–β–alumina . . . as electrolyte, Nafe, Solid state Ionics 68 (1994) Month unavailable, pp. 249–255.

The feasibility of a Potentiometric $CO_2$ sensor based on . . . conductivity of the electrolyte, Sensors and Activators B21, Nafe, (1994) Month unavailable, pp. 79–82.

* cited by examiner

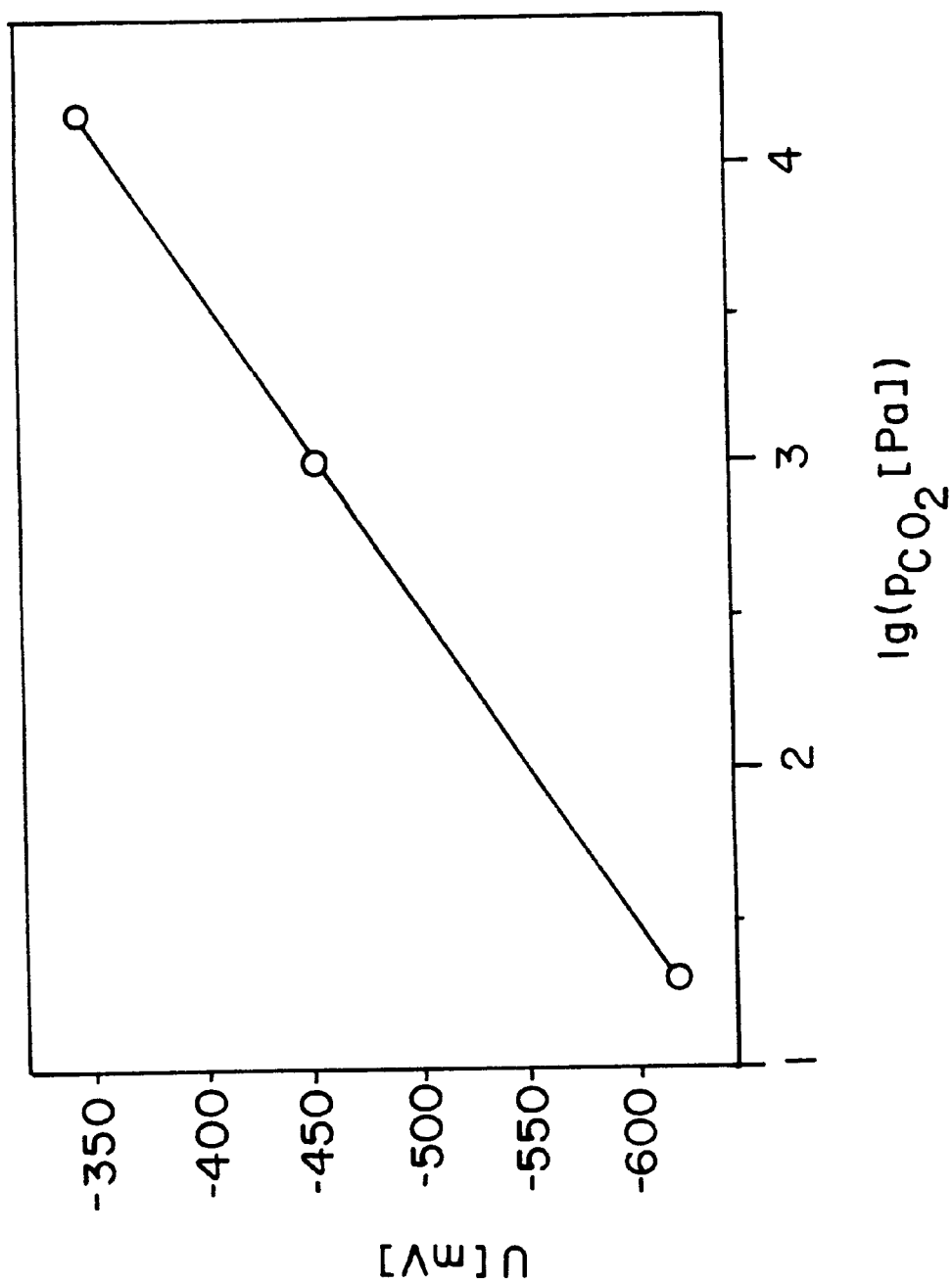

GAS SENSOR

The invention relates to a galvanic cell which is advantageously designed as a potentiometric sensor for determining gases such as $CO_2$, $SO_x$ and $NO_x$. The galvanic cell of the invention can be operated at elevated temperatures and is particularly well suited for applications in which the partial pressure of oxygen in the measuring medium varies with the content of the gases to be detected.

The use of oxygen-ion-conducting solid electrolytes for the potentiometric detection of gaseous anhydrides with the formula $XO_x$ (X=C, S, N) dates back to publications by Yamazoe and co-workers, who initially used the measuring principle to determine $SO_x$, (Yan et al., Chem. Lett. (1992), 635; Yan et al., Sensors and actuators B. 12 (1993), Yan et al., Sensors and Actuators B. 20 (1994), 81), and later also to detect $NO_x$ (Kurosawa et al., Solid State Ionics 79 (1995), 338; Miura et al., J. Electrochem. Soc. 143 (1996), L33) and $CO_2$ (Miura et al., Sensors and Actuators B., 24–25 (1995), 260).

The measuring principle used in these galvanic cells is based on the arrangement:

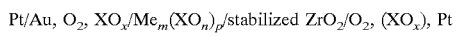

Pt/Au, $O_2$, $XO_x$/$Me_m(XO_n)_p$/stabilized $ZrO_2$/$O_2$, $(XO_x)$, Pt where Me is a metal such as Li, Na or K, and the stabilized $ZrO_2$ serves as oxygen-ion-conducting solid electrolyte (O-SE). The O-SE is coated on one side with platinum and on the other side with a gas-sensitive layer of the salt $Me_m(XO_n)_p$, or, in special embodiments, with a mixture of different salts of the gaseous anhydride to be detected. Both electrodes of the thus-prepared $ZrO_2$ pellet are in contact with the $O_2$- and $XO_x$-containing measuring gas.

According to Miura et al., vide supra, the functioning of the measuring electrode is based on the presence of a so-called ionic bridge. This ionic bridge, which provides an electrochemical connection between the metallic salt and the O-SE, is created by the formation of a solid phase containing both Me and oxygen ions.

The sensors proposed by the Yamazoe team have the disadvantage that the reproducible manufacture of functional examples thereof, ie, sensors that respond to the concentration of the gas to be detected, is difficult (cf. Yan et al., J. Electrochem. Soc. 143 (1996), 609). A sensor of this kind that does operate successfully is seemingly an exception due to a coincidental constellation. Our own research has shown that formation of the phase which is supposed to act as the ionic bridge is in fact unlikely for kinetic reasons, and that the electrodes used in the Yamazoe sensors do not respond at all to changes in the partial pressure of $CO_2$.

The use of an O-SE in connection with the potentiometric detection of gases was known even before Yamazoe and his co-workers published their work. The advantage which the direct contact between an O-SE and a salt of the gaseous anhydride to be detected—in the case in question a sulfate and a carbonate for the determination of $SO_x$ and $CO_2$ respectively—provides with respect to eliminating the effect of the partial pressure of oxygen was first pointed out by Kleitz et al. (New Types of Solid-Electrolyte Gas Sensors, in: P. Vashishta, J. N. Mundy, G. K. Shenoy (publ.), Fast Ion Transport in Solids, Elsevier North Holland Inc., New York 1979, 69) and by Belanger et al. (J. Electrochem. Soc. 131 (1984), 579). However, in these sensors the O-SE only served as an aid. The sensor signal responding to the content of the gas to be determined in the measuring medium drops exclusively at the salt which acts as metal-ionic conductor (Me-SE). The O-SE merely measures the difference in oxygen potential between the measuring gas and a reference gas. As a result of the direct contact between O-SE and Me-SE, the cell voltages of the two measuring cells add together and the overall signal is rendered independent of the oxygen pressure. The disadvantage connected with the provision of a reference gas is avoided in a sensor variant proposed later (Maruyama et al., Solid State Ionics 23 (1987), 107 and Saito et al., Solid State Ionics 28–30 (1988), 1644 and DE-OS 41 12 301). In this sensor variant, only the measuring gas is required to flow round the O-SE. Despite this, the sensor is still a combination of an oxygen and a metal-ion concentration cell, the only difference being that the two electrolytes in the sensor are sintered onto one another and thus form a so-called two-layer electrolyte. According to this measuring principle, the electronic conductivity of the metallic-ion conductor must be negligibly small compared with the ionic conductivity. In sensors of this kind, unlike those of Kleitz et al., vide supra, and Belanger et al., vide supra, where the salt itself serves as Me-SE, an independent material which is a comparatively better ionic conductor and which is in equilibrium with the salt $Me_m(XO_n)_p$ forms the measuring electrode.

The type of sensor described by Maruyama et al., vide supra, and Saito et al., vide supra, have the disadvantage that they are always a combination of a metallic-ion and an oxygen concentration chain. This is of special significance under the aspect of the non-negligible electronic conduction in the Me-SE (Näfe, Sensors and Actuators vol. 21 (1994), 79 and Näfe, Solid State Ionics 68 (1994), 249), which is usually associated with an impairment of the sensor measuring properties.

The object of the invention is thus the reproducible manufacture of a galvanic cell, especially a potentiometric sensor for detecting gases, which is based exclusively on an oxygen concentration chain incorporating an O-SE and which thus prevents the measuring properties of the sensor from being impaired by electron conduction in the electrolyte.

This object is established in that, between the oxygen-ion-conducting solid electrolyte and the metallic salt $Me_m(XO_n)_p$ acting as gas-sensitive layer, at least one intermediate layer of a material is introduced which seals off the potential-determining area of the solid electrolyte surface from the surroundings, making it impervious to gases therein, and which exhibits both high ionic conductivity (metallic ions Me) and high electronic conductivity; under the conditions in which the cell is used, the electronic conduction is preferably of a similar magnitude as or even greater than the ionic conduction. In addition, the material of the intermediate layer should preferably be inert under the conditions in which the sensor is operated and should allow the metal oxide $Me_yO$ to dissolve in it to a finite extent. The mobility of oxygen or the oxide $Me_yO$ in the material of the intermediate layer should be negligibly small.

One subject of this invention is thus a galvanic cell comprising:
a) an oxygen-ion-conducting solid electrolyte,
b) a gas-sensitive material which contains at least one salt having the structural formula $Me_m(XO_n)_p$, where Me is a metal, X stands for C, S or N, and the symbols m, n and p characterize the respective stoichiometric relations,
c) a material, interposed between the oxygen-ion-conducting solid electrolyte and the gas-sensitive material, which allows conduction both by cations of the metal Me and by electrons and which seals off a potential-determining area of the solid electrolyte surface from the surroundings, making it impervious to gases therein, and d) two electronically conductive potential taps at surface areas of the oxygen-ion-conducting solid electrolyte.

As oxygen-ion-conducting solid electrolyte, use may be made, for example, of a material based on $ZrO_2$, $ThO_2$, $CeO_2$, $HfO_2$ or $Bi_2O_3$. It is especially beneficial if, as oxygen-ion-conducting solid electrolyte, use is made of a material based on cubic, tetragonal or partially stabilized $ZrO_2$, eg, a $YO_{1.5}$-stabilized $ZrO_2$.

The salt with the structural formula $Me_m(XO_n)_p$ is preferably a salt of an alkali metal or an alkaline earth metal, eg, a Li, Na, K, Rb, Cs, Ca, Sr or Ba salt. The metallic salt is preferably a carbonate, sulfate or nitrate, depending on the gas to be detected.

The cationically conductive material may be an alkali-metal-ion or an alkaline-earth-metal-ion conductor, the electronic conductivity of which has preferably been raised intentionally above the usual level. This increase in electronic conductivity can be achieved, for example, by using a composite material which contains a mixture of an electronically conductive phase such as Pt and a cationically conductive phase. Alternatively, the electronic conductivity of the cationically conductive material can be increased by short-circuiting it electronically, eg, by attaching an additional potential tap between the gas-sensitive material and the cationic conductor, and connecting up this potential tap with one positioned between the cationic conductor and the solid electrolyte. Yet another alternative is to use materials which exhibit a sufficiently high cationic and also electronic conductivity.

Examples of suitable ionic conductors are the materials Nasicon and Lisicon, which are familiar Na- and Li-ion conductors, all metal-oxide-doped beta aluminates, and glasses, such as lithium silicate glass ($Li_2O:SiO_2$=1:2–4). To increase the electronic conductivity, these materials are preferably used in the form of a composite incorporating an electronically conductive phase; alternatively, they can be short circuited.

The galvanic cell of the invention is preferably used as a gas sensor, in particular for detecting $CO_2$, $NO_x$ and $SO_x$, both in trace quantities and in higher concentrations. The temperature range within which the sensor of the invention can be used is generally 450° C. to 750° C.

The invention is explained below with reference to FIGS. 1a, 1b and 2.

BRIEF DESCRIPTION OF THE DRAWINGS

FIG. 2 shows the sensitivity of the galvanic cell of FIG. 1 towards changing partial pressure of the measuring gas.

Figure 1A:
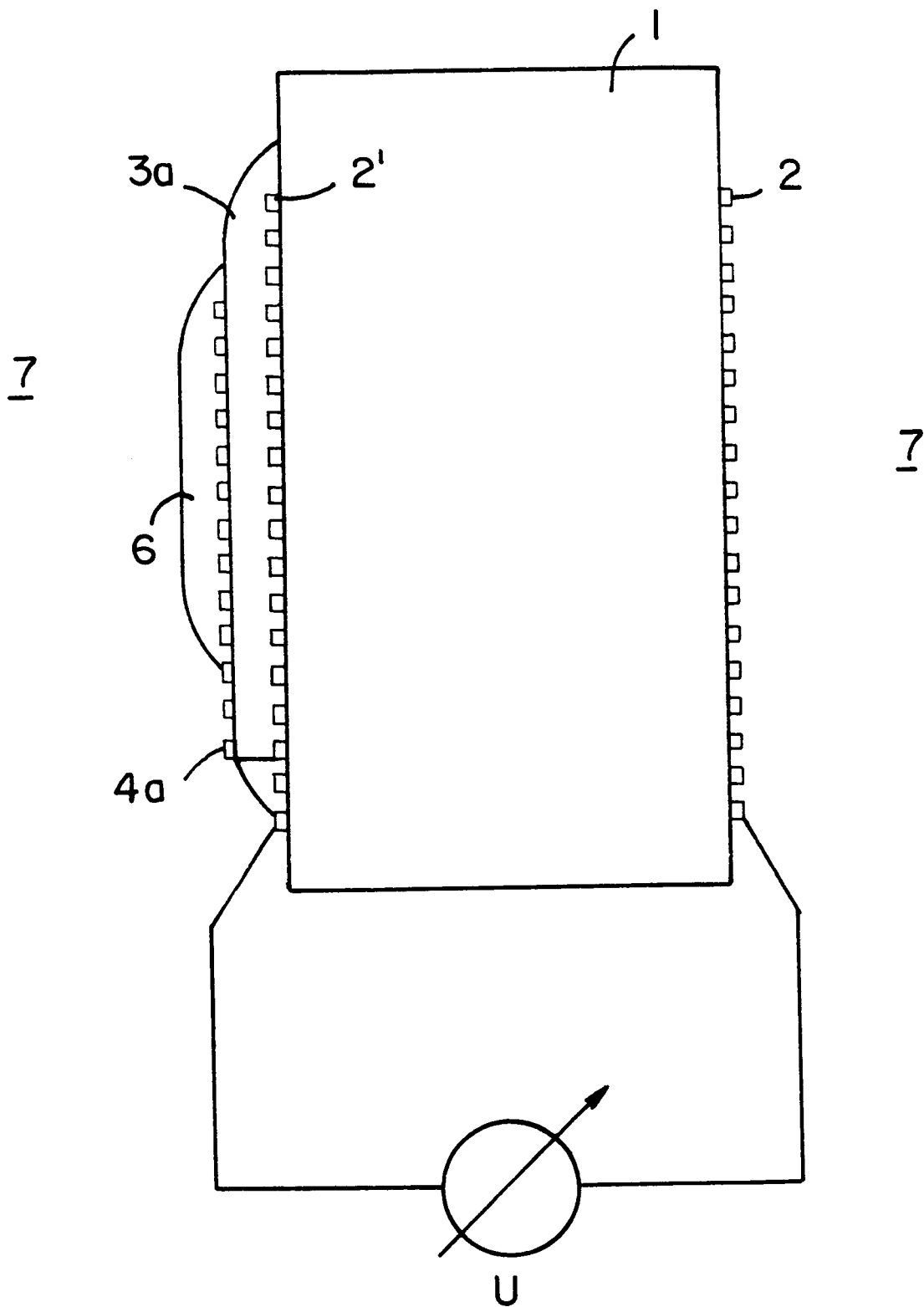
FIG. 1a shows a first embodiment of the galvanic cell according to the invention.
Figure 1B:
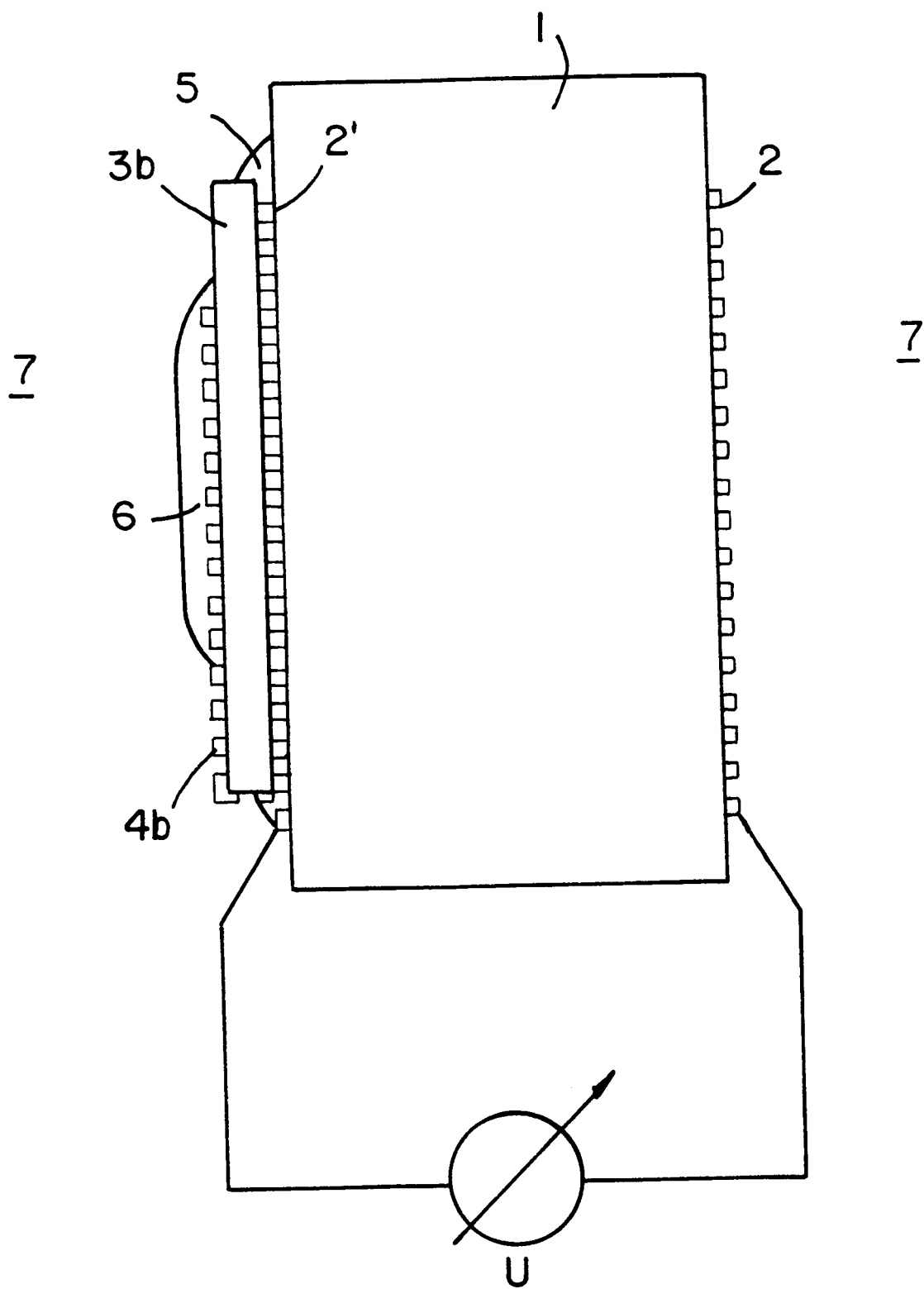
FIG. 1b shows a second embodiment of the galvanic cell according to the invention.

The basic assembly of a cell according to the invention is exemplified in FIGS. 1a and 1b. To both plane-parallel surfaces of the solid electrolyte (1), eg, a pellet of $YO_{1.5}$-stabilized $ZrO_2$, an electronically conductive tap (2,2') is applied. This may be effected, eg, by burning in a commercial platinum paste.

In the embodiment of the galvanic cell of the invention shown in FIG. 1a, a thin layer of a $Li_2O$-containing glass— eg, a lithium silicate glass—is melted onto one of these surfaces in such a manner that the glass layer (3a), through use of a precious-metal grid, eg, a gold grid (4a), is electronically short-circuited with the potential tap (2').

Alternatively, as shown in the embodiment of the galvanic cell of the invention shown in FIG. 1b, the glass (3a) can be substituted with a thin layer of a material (3b) which has been sintered to full density and is known to be cationically conductive, eg, by way of Li, Na or K ions. Examples of suitable materials for this purpose are Nasicon, Na- or K-beta-$Al_2O_3$, Lisicon, or a high melting Li glass.

An electronically conductive potential tap (4b) is applied to both sides of the cationic conductor. This is effected, eg, by coating the two plane-parallel surfaces with a layer of gold by means of vapour deposition. The two layers are preferably interconnected, ie, short-circuited, at the edge of the sintered body. Instead of this short-circuited body, use may be made of a composite body (not shown) which is both cationically and electronically conductive.

The cationically and electronically conductive sintered body (3b) prepared in this way is subsequently pressed onto one of the platinized surfaces—provided with the potential tap (2')—of the oxygen-ion-conducting solid electrolyte (1). This can be effected, for example, by using a drop of Na or K water-glass solution (5).

Application of the cationically and electronically conductive component (3a, 3b) has the effect of sealing off the potential-tap (2')-bearing surface of the oxygen-ion-conducting solid electrolyte, or a potential-determining area of said surface, from the surroundings such that it is impervious to gases contained therein.

To the conductor (3a, 3b), which allows conduction by ions of the metal Me and by electrons, a thin layer of a gas-sensitive salt $Me_m(XO_n)_p$ (6) is subsequently applied. This may be effected, for example, by applying a drop of saturated aqueous salt solution and letting it dry.

Both electrode surfaces of the oxygen-ion-conducting solid electrolyte are exposed to the measuring gas atmosphere (7), which contains the gas $XO_x$ to be determined and also $O_2$. The signal is measured across the platinized surfaces of the oxygen-ion-conducting solid electrolyte.

Sensor variants other than the above-described embodiment are of course possible. For example, to measure $CO_2$, use may also be made of the material combination $Cs_2CO_3$/Cs—ionic conductor and $Rb_2CO_3$/Rb—ionic conductor. To measure $SO_x$, use may be made, for example, of the combination $Me_2SO_4$/Me—ionic conductor (Me=Rb, Cs) and $MeSO_4$/Me—ionic conductor (Me=Ca, Sr, Ba). To measure $NO_x$, the combination $CsNO_3$/Cs—ionic conductor, for example, is suitable.

Instead of the compact assembly described in the embodiment, the sensor of the invention can also be made by means of planar technology.

FIG. 2, which shows how the cell voltage, measured at 680° C., varies as a function of the partial-pressure of $CO_2$, illustrates the sensitivity of a sensor prepared according to FIG. 1 towards changing $CO_2$ content of the measuring gas.

What is claimed is:

1. A galvanic cell comprising
   a) an oxygen-ion-conducting solid electrolyte,
   b) a gas-sensitive material which contains at least one salt having the structural formula $Me_m(XO_n)_p$, where Me is a metal, X stands for C, S or N, and the symbols m, n and p characterize the respective stoichiometric relations,
   c) a cationically conductive material, interposed between the oxygen-ion-conducting solid electrolyte and the gas-sensitive material, which allows conduction both by cations of the metal Me and by electrons, and which seals off a potential-determining area of the solid electrolyte surface from the surroundings, making the potential-determining area of the solid electrolyte surface impervious to gases therein, and d) two electronically conductive potential taps at surface areas of the oxygen-ion-conducting solid electrolyte wherein the cationically conductive and electronically conductive material comprises a composite material which contains a mixture of an electronically conductive phase and a cationically conductive phase and the cationically conductive and electronically conductive material comprises an electronically short-circuited cationic conductor.

2. The galvanic cell of claim 1, wherein the cationically conductive material is essentially chemically inert to the gas-sensitive material and the solid electrolyte.

3. The galvanic cell of claim 1, wherein the cationically conductive material comprises material in which an oxide $Me_yO$ of said Me is soluble.

4. A galvanic cell according to claim 1, wherein the cationically conductive material allows negligibly small mobility of at least one of oxygen and oxide $Me_yO$ of said Me.

5. A galvanic cell according to claim 1, wherein the oxygen-ion conducting solid electrolyte is an alkali metal ion conductor.

6. A galvanic cell according to claim 1, wherein the cationically conductive material is an alkaline earth metal ion conductor.

7. A galvanic cell according to claim 1, wherein the cationically conductive material is an alkali metal ion or alkaline earth metal ion conductor.

8. A galvanic cell according to claim 1, wherein the oxygen-ion-conducting solid electrolyte is selected from the group consisting of $ZrO_2$, $ThO_2$, $CeO_2$, $HfO_2$, and $Bi_2O_3$.

9. A galvanic cell according to claim 1, wherein the gas-sensitive material is a salt of an alkali metal or an alkaline earth metal.

10. A galvanic cell according to claim 1, wherein the salt is a carbonate, nitrate or sulfate.

11. A method for measuring a gas selected from the group consisting of carbon dioxide, a gaseous sulfuric oxide, and a gaseous nitrogen oxide, comprising contacting a sample with the galvanic cell of claim 1 to measure said gas in said sample.

* * * * *